United States Patent
Lisogurski et al.

(10) Patent No.: US 9,204,794 B2
(45) Date of Patent: Dec. 8, 2015

(54) MEDICAL DEVICE WITH ELECTRICALLY ISOLATED COMMUNICATION INTERFACE

(71) Applicant: Covidien LP, Mansfield, MA (US)

(72) Inventors: Daniel Lisogurski, Boulder, CO (US); Friso Schlottau, Lyons, CO (US); Jonathan Snyder, Northglenn, CO (US); Saba Bakhshi Khayani, Denver, CO (US); Andy S. Lin, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 356 days.

(21) Appl. No.: 13/741,105

(22) Filed: Jan. 14, 2013

(65) Prior Publication Data

US 2014/0199893 A1    Jul. 17, 2014

(51) Int. Cl.
*A61B 5/00* (2006.01)
*H01R 13/64* (2006.01)
*A61B 5/0205* (2006.01)
*A61M 16/04* (2006.01)
(Continued)

(52) U.S. Cl.
CPC .............. *A61B 5/00* (2013.01); *A61B 1/00124* (2013.01); *A61B 5/0205* (2013.01); *A61M 16/04* (2013.01); *A61M 16/0404* (2014.02); *A61M 16/0459* (2014.02); *A61M 16/0486* (2014.02); *H01R 13/64* (2013.01); *A61B 1/00018* (2013.01); *A61B 2562/182* (2013.01); *A61B 2562/227* (2013.01); *A61M 2016/1025* (2013.01); *A61M 2205/502* (2013.01); *A61M 2230/06* (2013.01); *A61M 2230/435* (2013.01); *H01R 24/62* (2013.01); *H01R 2201/12* (2013.01)

(58) Field of Classification Search
USPC ......................... 600/323, 301; 439/502, 909
IPC .. A61B 5/14551,5/14552; A61N 1/3752; H01R 31/06, 31/02, 2201/12, 13/5224
See application file for complete search history.

(56) References Cited

U.S. PATENT DOCUMENTS 6,193,655 B1 * 2/2001 McGrath ....................... 600/301
6,811,538 B2   11/2004 Westbrook et al.
(Continued)

FOREIGN PATENT DOCUMENTS

WO    WO2005110215       11/2005
WO    WO2005114524 A2   12/2005
(Continued)

OTHER PUBLICATIONS

Isolating USB. Maxim Integrated Products, Sep. 22, 2006.
(Continued)

*Primary Examiner* — Hien Vu
(74) *Attorney, Agent, or Firm* — Fletcher Yoder PC

(57) ABSTRACT

The present disclosure relates generally to medical devices and, more particularly, to medical devices with electrical connectors. In one embodiment, a medical device may include a medical connector having one or more contacts configured to enable communication between the medical device and a medical monitor according to a Universal Serial Bus (USB) standard. The medical connector may also include an interface region disposed at least partially about the one or more contacts. The interface region may be configured to physically couple to a mating connector of the medical monitor. Additionally, the interface region may include a geometry or a dimension that does not comply with the USB standard.

17 Claims, 7 Drawing Sheets

(51) Int. Cl.
  *H01R 24/62* (2011.01)
  *A61M 16/10* (2006.01)
  *A61B 1/00* (2006.01)

(56) References Cited

U.S. PATENT DOCUMENTS

| | | |
|---|---|---|
| 7,129,836 B2 | 10/2006 | Lawson et al. |
| 7,220,220 B2 | 5/2007 | Stubbs et al. |
| 7,297,119 B2 | 11/2007 | Westbrook et al. |
| 7,399,205 B2 * | 7/2008 | McNeely et al. .............. 439/577 |
| 7,428,432 B2 | 9/2008 | Al-Ali et al. |
| 7,500,950 B2 | 3/2009 | Al-Ali et al. |
| 2002/0101349 A1 * | 8/2002 | Rojas, Jr. .................... 340/573.1 |
| 2004/0113498 A1 | 6/2004 | Kroenke |
| 2005/0065417 A1 | 3/2005 | Al-Ali et al. |
| 2005/0075548 A1 | 4/2005 | Al-Ali et al. |
| 2005/0228244 A1 | 10/2005 | Banet |
| 2005/0247311 A1 | 11/2005 | Vacchiano et al. |
| 2005/0251056 A1 | 11/2005 | Gribkov et al. |
| 2006/0084878 A1 | 4/2006 | Banet et al. |
| 2006/0142808 A1 | 6/2006 | Pearce et al. |
| 2006/0155589 A1 | 7/2006 | Lane et al. |
| 2006/0220881 A1 | 10/2006 | Al-Ali et al. |
| 2006/0226992 A1 | 10/2006 | Al-Ali et al. |
| 2006/0238358 A1 | 10/2006 | Al-Ali et al. |
| 2006/0258926 A1 | 11/2006 | Al-Ali et al. |
| 2006/0265022 A1 | 11/2006 | John et al. |
| 2006/0282001 A1 | 12/2006 | Noel et al. |
| 2007/0049842 A1 | 3/2007 | Hill et al. |
| 2007/0071643 A1 | 3/2007 | Hall et al. |
| 2007/0123783 A1 | 5/2007 | Chang |
| 2007/0135866 A1 | 6/2007 | Baker et al. |
| 2007/0167694 A1 | 7/2007 | Causevic et al. |
| 2007/0208233 A1 | 9/2007 | Kovacs |
| 2007/0208262 A1 | 9/2007 | Kovacs |
| 2007/0208269 A1 | 9/2007 | Mumford et al. |
| 2007/0225606 A1 | 9/2007 | Naghavi et al. |
| 2007/0276261 A1 | 11/2007 | Banet et al. |
| 2007/0276262 A1 | 11/2007 | Banet et al. |
| 2007/0282478 A1 | 12/2007 | Al-Ali et al. |
| 2008/0030468 A1 | 2/2008 | Al-Ali et al. |
| 2008/0039701 A1 | 2/2008 | Al-Ali et al. |
| 2008/0077026 A1 | 3/2008 | Banet et al. |
| 2008/0091089 A1 | 4/2008 | Guillory et al. |
| 2008/0091090 A1 | 4/2008 | Guillory et al. |
| 2008/0097176 A1 | 4/2008 | Music et al. |
| 2008/0097177 A1 | 4/2008 | Music et al. |
| 2008/0108884 A1 | 5/2008 | Kiani |
| 2008/0114226 A1 | 5/2008 | Music et al. |
| 2008/0171311 A1 | 7/2008 | Centen et al. |
| 2008/0177160 A1 | 7/2008 | Al-Ali et al. |
| 2008/0189783 A1 | 8/2008 | Music et al. |
| 2008/0221418 A1 | 9/2008 | Al-Ali et al. |
| 2008/0224852 A1 | 9/2008 | Dicks et al. |
| 2008/0243021 A1 | 10/2008 | Causevic et al. |
| 2008/0316488 A1 | 12/2008 | Mao et al. |
| 2008/0319290 A1 | 12/2008 | Mao et al. |

FOREIGN PATENT DOCUMENTS

| | | |
|---|---|---|
| WO | WO2007070855 | 6/2007 |
| WO | WO2008073584 | 6/2008 |

OTHER PUBLICATIONS

Stewart, Brad. "Design of an Electrically Isolated USB Interface," Freescale Semiconductor, Inc., 2010.

* cited by examiner

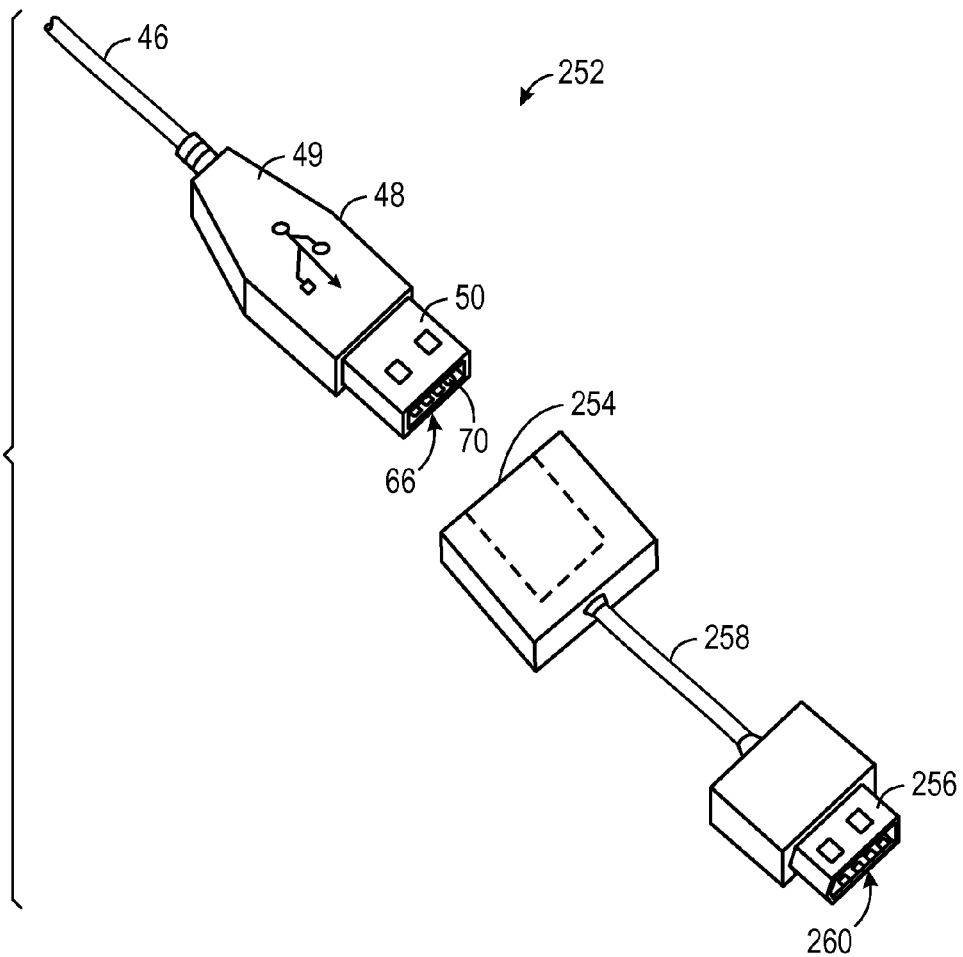

MEDICAL DEVICE WITH ELECTRICALLY ISOLATED COMMUNICATION INTERFACE

BACKGROUND

The present disclosure relates generally to medical devices and, more particularly, to medical devices with electrical connectors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. These medical devices provide doctors and other healthcare personnel with the information they need to provide the best possible healthcare for their patients. As a result, such medical devices have become an indispensible part of modern medicine.

The medical devices may communicate with a patient monitor using a communication cable and an electrical connector. For example, the medical device may be a pulse oximetry sensor, a regional oximetry sensor, an electrocardiography sensor, or a camera disposed about a tracheal tube. A medical device may use such an electrical connector to send a signal to a patient monitor for processing and/or display. For example, a visualization device (e.g., a camera) disposed about a tracheal tube may send a signal corresponding to an image obtained by the visualization device. Certain electronic medical devices (e.g., the tracheal tube with the visualization device) and their corresponding patient monitors may follow medical electrical equipment safety standards as set forth by International Electrotechnical Commission (IEC) 60601-1. For example, the patient monitor may include electrical isolation circuitry in accordance with IEC 60601-1. However, some medical devices may have electrical connectors, such as a universal serial bus (USB) connector, which enable connection with a variety of computing devices that may not necessarily include desired electrical isolation circuitry.

BRIEF DESCRIPTION OF THE DRAWINGS

Advantages of the disclosed techniques may become apparent upon reading the following detailed description and upon reference to the drawings in which:

FIG. 19 is a perspective view of a dongle configured to receive the connector of FIG. 1 and to connect with a mating connector of the medical monitor of FIG. 3 that is shaped to receive the dongle, in accordance with an aspect of the present disclosure.

DETAILED DESCRIPTION OF SPECIFIC EMBODIMENTS

Figure 1:
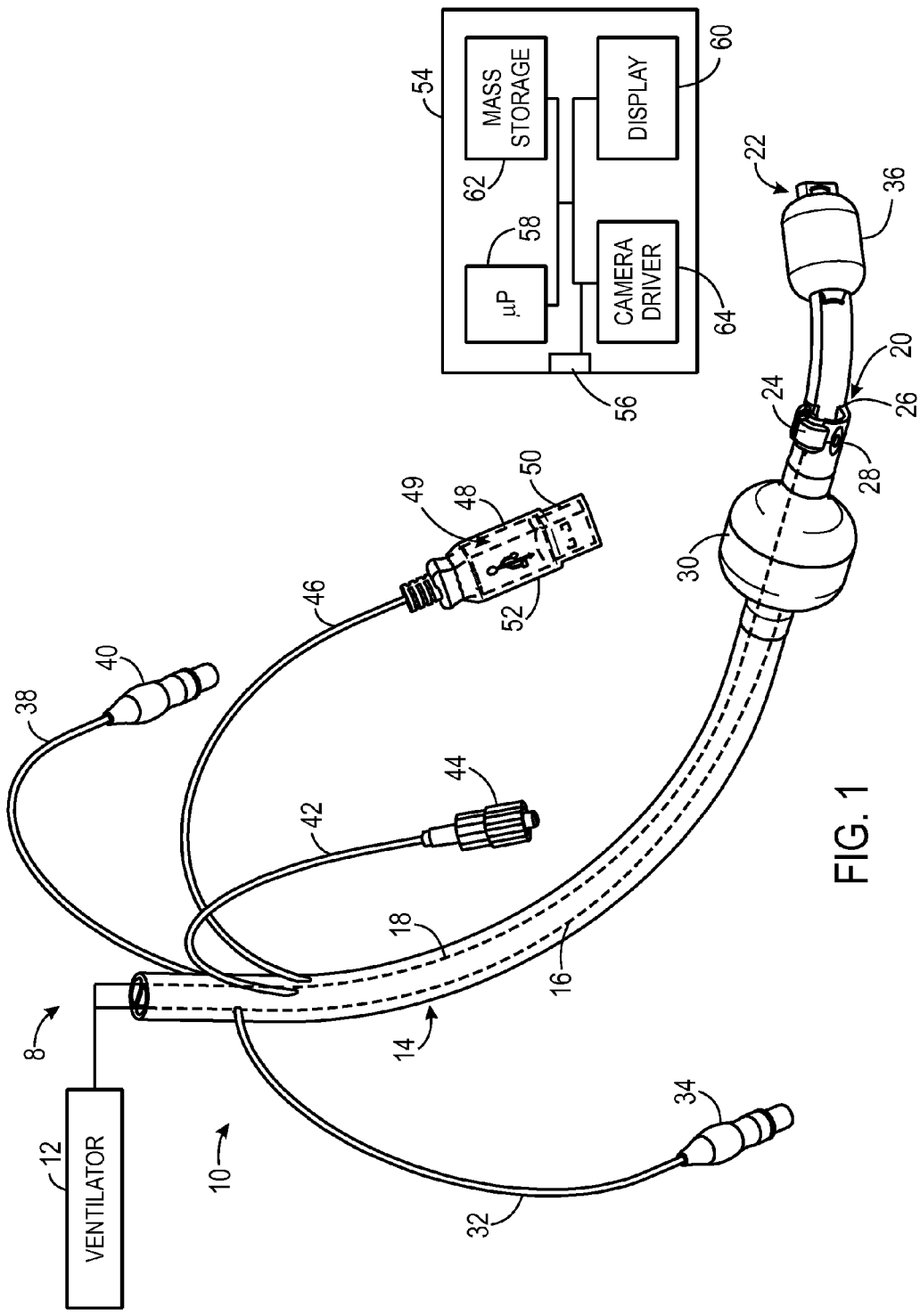
FIG. 1 is a system including an embodiment of an endotracheal tube having a connector and an insulating shroud in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed above, medical devices may include an electrical connector to enable communication with a medical monitor. As discussed herein, a medical monitor is defined as a computing device that is configured to monitor patient parameters or images of a patient and is in compliance with the medical electrical equipment safety standards set forth by IEC-60601-1. Specifically, as discussed herein, a medical monitor includes electrical isolation circuitry. Electrical isolation circuitry may control the flow of power from a medical monitor to a medical device. In one embodiment, electrical isolation circuitry may be configured to electrically isolate a patient from an earth ground.

Medical devices may connect and communicate with such a medical monitor using, for example, a standard USB connector. Indeed, USB connectors are widely available and inexpensive, which has led to their use in a variety of electrical devices, including many medical devices. Unfortunately, this also enables a medical device with a USB connector to connect with a laptop or powered USB hub that does not have electrical isolation circuitry in compliance with IEC-60601-1. Similarly, medical devices may include other standard connector types, such as a serial port connector, a video graphics array (VGA) connector, a D-subminiature connector, a BNC connector, or a mini-DIN connector, which may also connect with a non-medical computing device lacking such circuitry. Furthermore, some electrical connectors may have an exposed ground connection, or a configuration in which a person or object may inadvertently contact the pins of the connector.

To address these and other shortcomings of existing devices, the present embodiments include, among other approaches, a medical device having an electrical connector adapted (e.g., shaped) so as to connect specifically to medical monitors having electrical isolation circuitry. Generally, to enable the medical device to connect to specific medical monitors, the electrical connector of the medical device may be shaped such that the dimensions and/or geometry of the electrical connector do not comply with the USB standard. That is, the dimensions and/or shape of the electrical connector do not correspond with any of the connector types complying with the USB standard (e.g., the standard USB specification), such as the USB Series Standard-A, Standard-B, Mini-A, Mini-B, Micro-A, or Micro-B. For example, as discussed with respect to FIGS. 2, 4, 6, 8, 10, and 12, the medical device may be equipped with an asymmetrically-shaped insulating shroud that covers a connection region of the connector. Additionally, as discussed with respect to FIG. 13, the insulating shroud may be symmetrical, but may have dimensions or protrusions that do not comply with the USB standard. The connection region may be the portion of the connector configured to physically and electrically couple with a mating connector of a monitor (e.g., via one or more pins). As such, the insulating shroud may cover the connection region so as to block inadvertent contact with pins and/or an exposed ground connection of the connection region.

Further, the asymmetric geometry of the insulating shroud may limit connection to devices (e.g., medical monitors with isolation circuitry) having a mating connector with a receptacle for receiving the asymmetric geometry. Indeed, the asymmetric geometry may provide an indication to a user that a medical device may be appropriate for use with a particular medical monitor having the mating connector and the electrical isolation circuitry in accordance with IEC-60601-1. In addition, the asymmetric insulating shroud may provide a visual and/or tactile indication to a user regarding the correct orientation of the electrical connector to facilitate insertion into a mating connector.

It should be noted that, as discussed herein, the medical device may be any suitable medical device. By way of non-limiting example, medical devices in accordance with present embodiments may include a tracheal tube having one or more electrical components (e.g., a visualization device), a pulse oximetry sensor, a bispectral index (BIS) sensor, an electroencephalography (EEG) sensor, an electrocardiography (ECG) sensor, a surgical tool, or any combination of medical devices. An example endotracheal tube incorporating certain of the present approaches are discussed in further detail below with respect to FIG. 1.

A suitable medical monitor may be provided to connect with the electrical connector of the desired medical device. Accordingly, the medical monitor may include a receptacle shaped to receive the connection region and the insulating shroud of the connector. As such, an embodiment of a mating connector having the receptacle may correspond to an embodiment of a connection region and an insulating shroud of an electrical connector. For example, embodiments of asymmetrically-shaped connectors and corresponding mating connectors are discussed with respect to FIGS. 4 and 5, FIGS. 6 and 7, FIGS. 8 and 9, and FIGS. 10 and 11.

In certain circumstances, it may be desirable to connect the medical device with the asymmetric shroud to a non-medical computing device. For example, a healthcare provider may desire to view images generated from an endotracheal visualization device, or view data stored on the device, on a portable computing device such as a personal data assistant (PDA), a tablet computer, a laptop computer, or the like. However, typical portable computing devices may lack the electrical isolation circuitry suitable for compliance with IEC 60601-1 and, therefore, may lack a mating connector suitable for connecting to an embodiment of the asymmetric connectors described herein. Accordingly, an embodiment of the present disclosure, which is discussed in further detail below with respect to FIG. 12, relates to an adaptor having the electrical isolation circuitry that enables connection between two types of electrical connectors. For example, the adaptor may be configured to receive the asymmetric insulating shroud of the electrical connector and also to connect with a standard portable computing device (e.g., plug into a standard USB port of a laptop).

In addition to, or in lieu of, providing an insulating shroud having an asymmetric geometry to induce asymmetry into the connector, a connection region of an electrical connector may have an asymmetric geometry or symmetric geometry. Similar to the insulating shroud, in some embodiments, the dimensions and/or shape of the connection region may not comply with the USB standard. An embodiment of such an asymmetric electrical connector and a mating connector of a medical monitor having a corresponding asymmetric geometry is discussed below with respect to FIG. 16-18.

In other embodiments, the medical device may be equipped with a standard electrical connector, such as a USB connector in compliance with the USB standard. However, it may be desirable to connect the medical device to a medical monitor having a mating connector that does not comply with the USB standard. Accordingly, an embodiment of the present disclosure, which is discussed in further detail below with respect to FIG. 17, relates to a dongle that may be an interface between the medical device and the medical monitor. For example, the dongle may be configured to receive the electrical connector of the medical device and to connect to the mating connector of the medical monitor.

As noted above, connectors in accordance with the present techniques may be used in conjunction with any medical device having one or more electrical components. One such medical device is illustrated in FIG. 1, which is a perspective view of a system 8 including an embodiment of a tracheal tube 10 configured to be placed in a patient bronchial stem. The tracheal tube 10 may be used in conjunction with an acceptable auxiliary airway device, such as a ventilator 12. The tracheal tube 10 includes a central tubular body 14 with a tracheal ventilation lumen 16 and a bronchial ventilation lumen 18. The tracheal ventilation lumen 16 terminates at a tracheal lumen distal end 20 while the bronchial ventilation lumen 18 terminates in a bronchial lumen distal end 22. The tube 10 may include a visualization device 24 (e.g., a sensor) associated with one or both of the tracheal ventilation lumen 16 and the bronchial ventilation lumen 18.

The tracheal lumen distal end 20 of ventilation lumen 16 terminates in an opening 26 and may be placed in a patient trachea during operation to maintain airflow to and from the patient's lungs. A Murphy's eye 28 may be present and located on the ventilation lumen 16 opposite the opening 26 to prevent airway occlusion. As illustrated, a tracheal cuff 30 may encircle the tubular body 14 and be inflated to seal against the walls of a body cavity (e.g., a trachea). The cuff 30 may be inflated via an inflation lumen terminating in an inflation tube 32 connected to an inflation pilot balloon and valve assembly 34. The bronchial ventilation lumen 18 may include a bronchial inflation cuff 36 that is configured to seal against the walls of a patient's bronchus. The cuff 36 may be inflated via an inflation lumen terminating in an inflation tube 38 connected to an inflation pilot balloon and valve assembly 40. In certain embodiments, the cuff 30 or cuff 36 may be generally sized and shaped as a high volume, low pressure cuff that may be designed to be inflated to pressures between about 15 cm $H_2O$ and 30 cm $H_2O$.

The tubular body 14 and the cuffs 30 and 36 may be formed from any suitable materials having desirable mechanical properties (e.g., puncture resistance, pin hole resistance, tensile strength, and so forth) and desirable chemical properties (e.g., biocompatibility). Portions of the visualization device 24 may be formed from the same material or different materials as the tube 10. Generally, the visualization device 24 may be formed from biocompatible polymers and other non-reactive materials. The visualization device 24 may be adhered to or fastened to the tubular body 14 by any suitable process. For example, the visualization device 24 may be embedded in or adhered (e.g., welded) to the tubular body 14. The tube 10 may also include a fluid delivery lumen 42 in communication with the visualization device 24. The fluid delivery lumen 42 may terminate in a proximal coupler 44 that is sized and shaped to connect to a fluid source (e.g., a saline reservoir, a syringe). A portion of the fluid delivery lumen 42 may be formed within a wall of the tube 10. The fluid delivery lumen 42 may be configured to flush or clear mucus buildup on the visualization device 24.

The tube 10 may also include a cable 46 coupled to the visualization device 24. Generally, the cable 46 is configured to enable communication between the visualization device 24 and an external device, such as a medical-grade monitor, as discussed in further detail below. The cable 46 may run along or within (e.g., in a dedicated lumen) the tubular body 14. The cable 46 may terminate in an electrical connector 48 (e.g., a USB connector), which may include a body 49 and a connection region 50 protruding from the body 49. The connection region 50 may be the portion of the electrical connector 48 configured to physically couple to a mating connector of a computing device. For example, in an embodiment in which the electrical connector 48 is a USB connector, the body 49 may be the plastic portion that a user may handle and the connection region 50 may be defined by the metal portion that is inserted into a corresponding mating connector. Furthermore, the connection region 50 may at least partially surround one or more pins (e.g., for electrically coupling to a mating connector) of the electrical connector 48.

While a USB connector is depicted in FIG. 1, it should be appreciated that the electrical connector 48 may be any type of electrical connector suitable for communicating with or receiving power from a computing device. For instance, the electrical connector 48 may be a serial port connector, a video graphics array (VGA) connector, a D-subminiature connector, a BNC connector, or a mini-DIN connector. Furthermore, the electrical connector 48 may be a male or female connector.

In accordance with embodiments of the present disclosure, the electrical connector 48 may include an insulating shroud 52 covering the connection region 50. The insulating shroud 52 may extend past the connection region 50 to block a user from inadvertently contacting the connection region 50 and/or one or more pins disposed within the connection region 50. That is, in certain embodiments, the electrical connector 48 with the insulating shroud 52 may be touchproof such that inadvertently contacting the electrical connector 48 to any surface may not ground the patient (i.e., cause a voltage to run through the patient). The insulating shroud 52 may physically couple to a mating connector of a computing device. As such, at least a portion of the insulating shroud 52 may be defined as an interface region. Specifically, the interface region of the insulating shroud 52 will include one or more surfaces sharing a common boundary with one or more surfaces of a mating connector of the computing device. The insulating shroud 52 may be asymmetrically shaped to limit connection to the mating connector of the computing device having certain attributes, such as electrical isolation circuitry. One example of such a device, as discussed below, is a medical monitor. Additionally, in certain embodiments, the asymmetric geometry of the insulating shroud 52 may provide an indication to a user (e.g., a caregiver) regarding the correct orientation of the electrical connector 48 to facilitate insertion into a corresponding mating connector.

Again, the connector 48, in certain embodiments, may be shaped so as to connect only to computing devices having a mating connector with a matching geometry (e.g., a medical monitor) and may be shaped such that the connector 48 does not comply with the USB standard. The matching geometry of the connector may serve as an indicator that the computing device includes particular features, such as electrical isolation circuitry. Accordingly, the illustrated system 8 also includes a monitor 54 having a mating connector 56 configured to physically and electrically couple to the connector 48. Generally, the monitor 54 is configured to monitor patient parameters, such as by receiving and processing signals generated via the visualization device 24. In particular, the monitor 54 may be coupled to the visualization device 24 via the connectors 48, 56 and the cable 46. As discussed below, the mating connector 56 may include one or more pins (FIG. 5) to enable communication with one or more pins of the electrical connector 48.

The monitor 54 may be a stand-alone device or may, in certain embodiments, be integrated into a single device with, for example, the ventilator 12. In addition to electrical isolation circuitry in accordance with IEC 60601-1, the monitor 54 may include processing circuitry, such as a microprocessor 58 coupled to an internal bus and a display 60. By way of example, the monitor 54 may receive one or more signals representative of image data collected by the visualization device 24, and may process the image data using the microprocessor 58. The data may be stored in a mass storage device 62, such as RAM, PROM, optical storage devices, flash memory devices, hardware storage devices, magnetic storage devices, or any suitable computer-readable storage medium. The data may be accessed and operated upon according to microprocessor 58 instructions.

For example, the monitor 54 may be configured to process data received from the visualization device 24 and provide indications of tube placement within the trachea. The indications may include audio, visual or other user-perceivable indications. In certain embodiments, the monitor 54 may be configured to communicate the information to another device, such as the ventilator 12. The monitor 54 may also provide camera drive signals (including a drive signal to any associated light sources) to the visualization device 24 via camera driver 64. Further, the monitor 54 may also be configured to control the delivery of fluid or air via the fluid delivery lumen 42. In certain embodiments, the monitor 54 may supply power to electrically-powered elements of the tube 10, such as the visualization device 24, via the connectors 48, 56.

Figure 2:
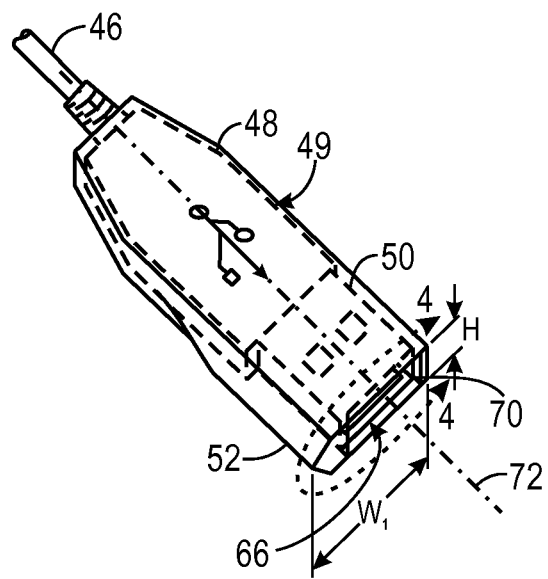
FIG. 2 is a perspective view of the connector and the insulating shroud of FIG. 1 and including a connection region of the connector and a connection axis centered about a front cross-section of the connection region in accordance with an aspect of the present disclosure.

As noted above, the electrical connector 48 of the tube 10 may physically and electrically couple to the mating connector 56 of the monitor 54. Accordingly, as illustrated in FIG. 2, the connection region 50 may include a USB pin-out 66 that includes one or more pins 70 (e.g., one or more electrical contacts), which are described in further detail below with respect to FIG. 4, to enable the electrical connection to the one or more corresponding pins of the mating connector 56 of the monitor 54. It should be noted that in embodiments in which the electrical connector 48 is not a USB connector, the electrical connector 48 may include a different pin-out 66 and/or a different configuration of the pins 70. Specifically, the electrical connector 48 may connect with the mating connector 56 along a connection axis 72. The connection axis 72 may be centered about a front cross-section of the connection region 50 such that the connection axis 72 is a longitudinal axis of the electrical connector 48. Furthermore, it should be appreciated that the configuration of the connection region 50 and pins 70 may vary across different connector types. Accordingly, both the geometry and the pin configuration of the mating connector 56 may change for the various connector types to facilitate the physical and electrical coupling with electrical connector 48 along the connection axis 72. Various non-limiting examples of different geometries of the connection region 50 and of the mating connector 56 are discussed below with respect to FIGS. 4, 6, 8, 10, 12-14, 16, and, 17 and FIGS. 5, 7, 9, 11, and 18, respectively.

In addition to the components that enable communication, the illustrated electrical connector 48 also includes the insulating shroud 52. The insulating shroud 52 may cover the connection region 50, and may partially or entirely cover the body 49 of the electrical connector 48. The insulating shroud 52 may be fixed or removable. In embodiments where the insulating shroud 52 is fixed, the insulating shroud 52 may be adhered to or may be integral with the body 49. In one embodiment, the insulating shroud 52 may be retractable, such that as a user inserts the electrical connector 48 into a mating connector, the insulating shroud 52 abuts a surface surrounding the mating connector and retracts, allowing the connection region 50 to be inserted into a receptacle of the mating connector.

Additionally, the insulating shroud 52 may cover the connection region 50 such that the connection region 50 is recessed in the insulating shroud 52. The recessed configuration may reduce the possibility of inadvertent contact with the connection region 50 and/or the pins 70. Specifically, the recessed configuration may block a user from touching the connection region 50 and/or the pins 70, and may provide an insulating barrier between the connection region 50 and/or the pins 70 and a grounded surface. The insulating shroud 52 may be formed from any suitable material with insulating properties such as an insulating polymer, plastic, rubber, glass, ceramic, or paper. In certain embodiments, the insulating material of the insulating shroud 52 may be transparent such that the connection region 50 and the configuration of the pins 70 may be visible to a user to facilitate recognition of the connector type. This may enable a user to more quickly select the appropriate mating connector for the electrical connector 48.

The insulating shroud 52 may also be shaped to enhance usability. For example, the insulating shroud 52 may be shaped such that a user may more easily determine the correct orientation of the electrical connector 48 for connection with the mating connector 56 of the monitor 54. This may be useful, for example, in high-stress and/or time-critical medical environments in which a healthcare provider may not have sufficient time to examine the electrical connector 48 for indicia (e.g., the USB insignia) to determine its correct orientation for connection. To address this issue, the insulating shroud 52 may have an asymmetric geometry (e.g., a triangular protrusion along one side) that may connect with mating connector 56 with a corresponding asymmetric geometry. As such, a user may be able to quickly connect the electrical connector 48 with mating connector 56.

As noted above, the insulating shroud 52 and/or the connection region 50 may be shaped to create various asymmetric geometries and/or symmetric geometries that do not comply with the USB standard. Embodiments in which the connection region is asymmetric are discussed in detail below with respect to FIGS. 16 and 17. It should be noted that the insulating shroud 52 may have an inner and an outer geometry, and the geometries may be distinct. Generally, the outer geometry may be asymmetric with respect to a plane oriented along the connection axis 72 and bisecting a width of the connection region 50. Indeed, as highlighted by line 4-4, the geometry of the front view of the insulating shroud 52 and/or the entirety of the insulating shroud 52 may be modified according to various embodiments, which will be described in further detail below with respect to FIGS. 4, 6, 8, 10, and 12-14.

Figure 3:
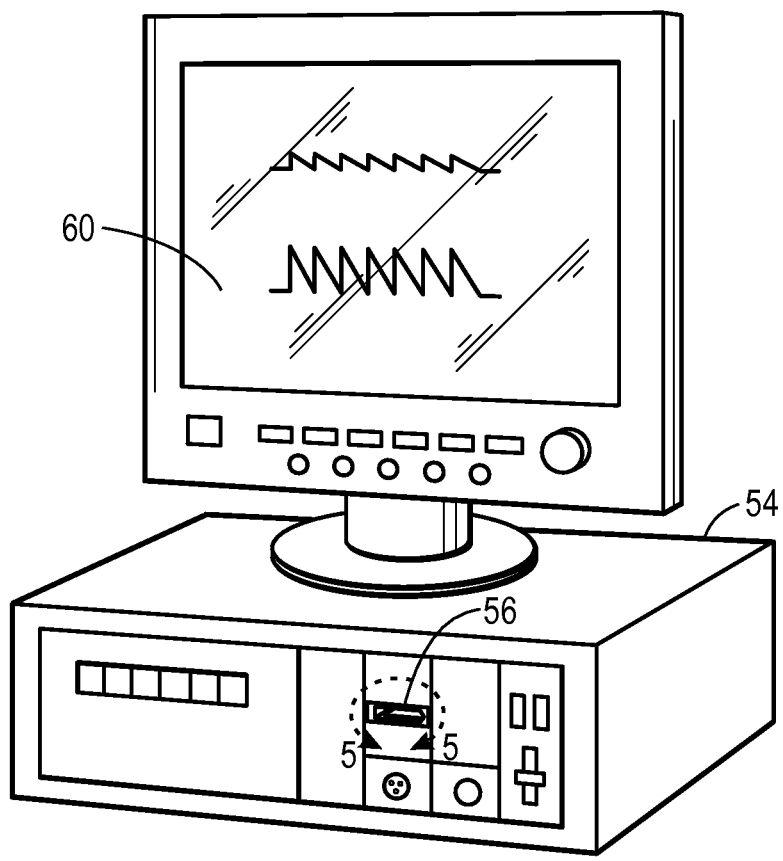
FIG. 3 is a perspective view of an embodiment of a medical monitor having a mating connector and a receptacle shaped to receive the connector and the insulating shroud of FIG. 2 along the connection axis in accordance with an aspect of the present disclosure.

Further, the mating connector 56 of the monitor 54 and its corresponding receptacle may be adjusted to accommodate the various embodiments of the insulating shroud 52 and the connection region 50. Indeed, as highlighted by line 5-5 of FIG. 3 and as will be discussed in more detail below with respect to FIGS. 5, 7, 9, and 11, the receptacle and the mating connector 56 of the monitor 54 may be adjusted for the geometries of corresponding embodiments of the insulating shroud 52 and the connection region 50 as illustrated in FIGS. 4, 6, 8, and 10, respectively. Furthermore, in certain embodiments, the mating connector 56 may include a structure sized to fit about the connection region 50. By way of non-limiting example, in embodiments in which the mating connector 56 is a female USB connector, the mating connector 56 may fit about the corresponding male connection region 50. Conversely, in embodiments in which the mating connector 56 is a male USB connector, the connection region 50 may fit about the mating connector 56.

As noted above, FIG. 4 illustrates an embodiment of the front view (e.g., a view along the connection axis 72) of the insulating shroud 52. In some embodiments, the insulating shroud 52 may extend past the connection region 50 such that the connection region 50 is recessed within the insulating shroud 52. In the illustrated embodiment, however, the inner geometry 74 is flush with the connection region 50. Further, there may be a slight gap between the inner geometry 74 and the connection region 50 such that the mating connector 56 may fit about the connection region 50. The insulating shroud 52 may have an inner geometry 74 and an outer geometry 76. As illustrated, inner geometry 74 may be symmetric about a plane crosswise to the connection axis 72 (e.g., a plane bisecting a side of the inner geometry 74). However, embodiments in which the inner geometry 74 is asymmetric about such a plane are also presently contemplated.

Figure 4:
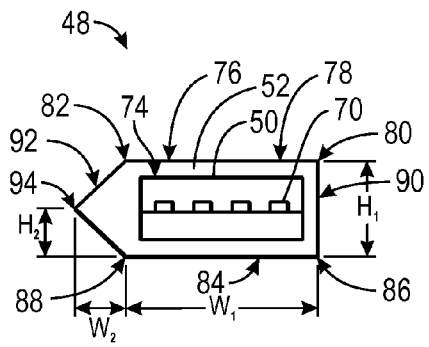
FIG. 4 is a front view of an embodiment of the connector and the insulating shroud of FIG. 2 illustrating an asymmetric geometry of the insulating shroud in accordance with an aspect of the present disclosure.

As illustrated in FIG. 4, at least one side of the outer geometry 76 may be angled with respect to the connection region 50 to induce asymmetry into the outer geometry 76. In particular, the outer geometry 76 may include a first surface 78, terminating at a first end 80 and a second end 82, and a second surface 84, terminating at a third end 86 and a fourth end 88. As illustrated, the first surface 78 is an opposing surface with respect to the second surface 84, and vice versa. As defined herein, an opposing surface is a face that is disposed across the connection region 50 from a recited surface (e.g., the other of a pair of opposing surfaces). Though other surfaces may also be handled, the first surface 78 and the second surface 84 may be handling surfaces that a user would likely grip when connecting the electrical connector 48 to the mating connector 56. The first surface 78 and the second surface 84 may have equal lengths, illustrated by $w_1$. The outer geometry 76 may additionally include a third surface 90 connecting the first end 80 and the third end 86. The third surface 90 may be substantially perpendicular to the first and second surfaces 78, 84 and the second surface 84 and may have a length illustrated by $h_1$. Additionally, the outer geometry 76 may include an angled (e.g., cornered) fourth surface 92 connecting the second end 82 and the fourth end 88. Accordingly, the third surface 90 is an opposing surface with respect to the fourth surface 92. Generally, asymmetry may be induced in the insulating shroud 52 by providing a surface that is not substantially parallel to its opposing surface. In the illustrated embodiment, for example, the cornered fourth surface 92, which is angled away from the connection region 50, is not parallel to the third surface 90, which is not angled with respect to the connection region 50.

Furthermore, the cornered fourth surface 92 may be longer than the third surface 90 to induce asymmetry in the insulating shroud 52. Specifically, in the illustrated embodiment, the cornered fourth surface 92 may include a corner 94 such that the fourth surface 92 may be a triangular protrusion. Indeed, in the illustrated embodiment, the fourth surface 92 includes two sides. Conversely, the first, second, and third surfaces 78, 84, 90 include only one side. As illustrated, the triangular protrusion may have dimensions of $h_2$ and $w_2$, where $w_2$ corresponds to the distance that the cornered fourth surface 92 protrudes from the second end 82 and the fourth end 88. Further, $h_2$ may be less than $h_1$ and may correspond to the distance between the corner 94 and the fourth end 88. In certain embodiments, $h_2$ may be 0-100%, 20-80%, or 40-60% of $h_1$. Similarly, $w_2$ may be 0-100%, 20-80%, or 40-60% of $w_1$. Furthermore, in certain embodiments, the angle of the corner 94 may be between 0-90°, 20-70°, or 40-50°. It should be noted that adjusting the dimensions of $h_2$ and/or $w_2$ may adjust the angle of the corner 94. Additionally, the illustrated outer geometry 76 is asymmetric with respect to a plane crosswise to the connection axis 72 and that bisects $w_1$. Furthermore, while illustrated as a triangular protrusion, in certain embodiments, the fourth surface 92 may be a triangular recess, or any surface having any number of sides.

Figure 5:
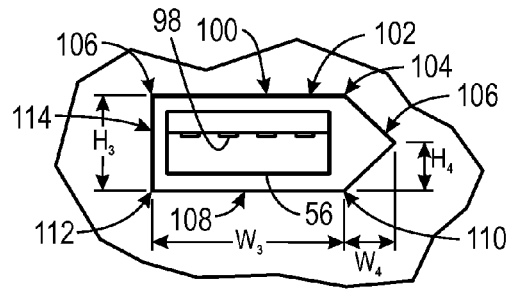
FIG. 5 is a front view of an embodiment of the mating connector and the receptacle of FIG. 3 illustrating an asymmetric geometry of the receptacle shaped to receive the connector and the insulating shroud of FIG. 4 along the connection axis in accordance with an aspect of the present disclosure.

FIG. 5 illustrates a front view of a portion of the monitor 54 having the mating connector 56. The mating connector 56 may include a USB pin-out 96 that includes one or more pins 98 (e.g., one or more electrical contacts) that may electrically couple with the pins 70 of the connector 58 to enable communication, power transmission, and so forth. Additionally, the monitor 54 may include a receptacle 100 surrounding the mating connector 56 to receive the outer geometry 76 of the insulating shroud 52 as described above. Thus, the insulating shroud 52 may be inserted into the receptacle 100 to enable the one or more pins 70 of the electrical connector 48 to couple with the one or more pins 98 of the mating connector 56. It should be appreciated that the geometry of the receptacle 100 may, in some embodiments, be mirrored with respect to the outer geometry 76. As illustrated, the receptacle 100 may have dimensions $h_3$, $w_3$, $h_4$, and $w_4$. The dimensions $h_3$, $w_3$, $h_4$, and $w_4$ may be approximately equal to $h_1$, $w_1$, $h_2$, and $w_2$ (e.g., the dimensions of the receptacle may be slightly greater to accommodate the insertion of the insulating shroud 52). Similar to the outer geometry 76, the receptacle 100 may include a first surface 102, terminating at a first end 104 and a second end 106, and a second surface 108, terminating at a third end 110 and a fourth end 112. The receptacle 100 may include a third surface 114 connecting the second end 106 and the fourth end 112 (e.g., to mirror the outer geometry 76), and a fourth surface 116 connecting the first end 104 and the third end 110. The fourth surface 116 may additionally include a corner corresponding to the corner 94.

Figure 6:
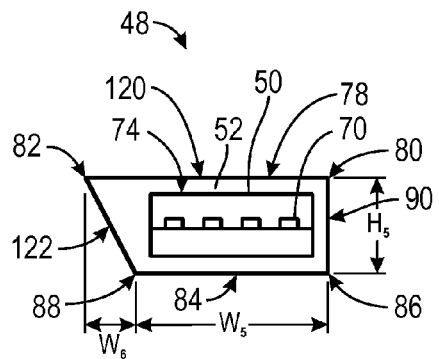
FIG. 6 is a front view of an embodiment of the connector and the insulating shroud of FIG. 2 illustrating an asymmetric geometry of the insulating shroud, in accordance with an aspect of the present disclosure.

As set forth above, the insulating shroud 52 may have a variety of geometries. As illustrated in FIG. 6, the insulating shroud 52 may have an outer geometry 120 including a slanted surface in addition to, or in lieu of, a cornered surface. In particular, the outer geometry 120 may include a slanted fourth surface 122 connecting the second end 82 and the fourth end 88. The slanted fourth surface 122 may be longer than the third surface 90, resulting in the first surface 78 and the second surface 84 having different lengths.

In the illustrated embodiment, the second surface 84 is longer than the first surface 78, though the opposite relationship is also presently contemplated. Specifically, the second surface 84 has a width of $w_5$, and the first surface 78 is longer by $w_6$ due at least to the angle by which the fourth surface 122 is slanted. As illustrated, the width the first surface 78 is equal to the sum of $w_5$ and $w_6$. In certain embodiments, $w_6$ may be 0-100%, 20-80%, or 40-60% of $w_5$. As may be appreciated, adjusting $w_6$ will adjust the angle at which the slanted fourth surface 122 is offset from being perpendicular to the first and second surfaces 78, 84.

As noted above, the shape of the fourth surface 122 induces asymmetry into the insulating shroud 52. In particular, the outer geometry 120 is asymmetrical with respect to a plane crosswise to the connection axis 72 and that bisects $w_5$. Additionally, the outer geometry 120 is asymmetrical with respect to a plane that bisects a width of the third surface 90, $h_5$. The asymmetry with respect to two planes, rather than one, of the insulating shroud 52 may advantageously facilitate a user's recognition of the correct orientation of the electrical connector 48 for connection with a corresponding mating connector (e.g., the mating connector 56 of the monitor 54).

Figure 7:
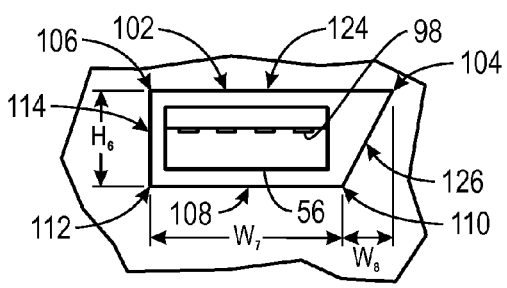
FIG. 7 is a front view of an embodiment of the mating connector and the receptacle of FIG. 3 illustrating an asymmetric geometry of the receptacle shaped to receive the connector and the insulating shroud of FIG. 6 along the connection axis, in accordance with an aspect of the present disclosure.

The monitor 54 may include a receptacle 124 to facilitate connection between the mating connector 56 and the electrical connector 48 having the outer geometry 120, as illustrated by FIG. 7. As described above, the receptacle 124 may be shaped with dimensions corresponding to the outer geometry 120 to enable the insertion of the insulating shroud 52 into the receptacle 124. Additionally, as with certain embodiments described above, the receptacle 124 may have surfaces and ends which are mirrored with respect to the outer geometry 120. Specifically, the receptacle 124 may have a slanted fourth surface 126 which may correspond to the slanted fourth surface 122 of the outer geometry 120. For example, $w_7$ and $w_8$ may be substantially the same as $w_5$ and $w_6$, respectively (allowing for some tolerance to receive the electrical connector 48).

Figure 8:
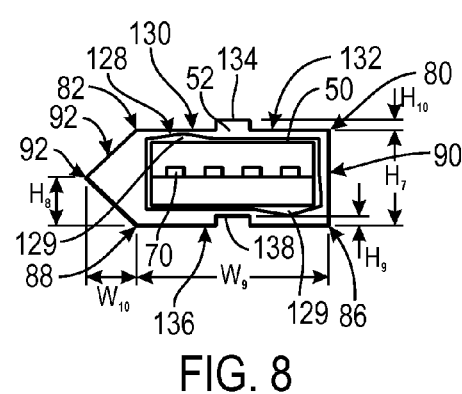
FIG. 8 is a front view of an embodiment of the connector and the insulating shroud of FIG. 2 illustrating an asymmetric geometry of the insulating shroud, in accordance with an aspect of the present disclosure.

In addition to, or as an alternative to, having an asymmetric outer geometry, the inner geometry of the insulating shroud 52 may be asymmetric. FIG. 8 is a front view of the insulating shroud 52 including such an inner geometry 128. As illustrated, the inner geometry 128 may be outwardly curved with respect to the connection region 50 in two regions of the insulating shroud 52. Again, there may be a slight separation between an inner geometry of the insulating shroud 52 and the connection region 50 to facilitate connection with a mating connector. As illustrated, the inner geometry 128 includes two triangular separations 129 disposed about opposite corners of the connection region 50. Thus, the inner geometry 128 may be asymmetric with respect to a plane crosswise to the connection axis 72 and bisecting the width of the connection region 50, as well as a plane crosswise to the connection axis 72 and bisecting the height of the connection region 50.

Additionally, as illustrated, an outer geometry 130 of the insulating shroud 52 may include one or more irregular surfaces, such as a ridge and/or a groove. Providing a ridge and/or a groove may help a user to determine the correct orientation of the electrical connector 48 for connection. By way of non-limiting example, a user may recognize a ridge by sight and/or touch and determine that the ridge corresponds to a particular surface (e.g., a top handling surface). For example, as illustrated, a first surface 132 of the outer geometry 130 may include a ridge 134 (e.g., a tab or a protrusion). Additionally, a second surface 136 of the outer geometry 130 may include a groove 138.

While the insulating shroud 52 is illustrated as having one groove and one protrusion, it should be noted that any one or a combination of the surfaces may have any one or a combination of grooves, protrusions, slants, curves, and so on. Further, the grooves, protrusions, etc., may generally have any desirable size and shape. For example, the groove 138 may protrude into the second surface 136 by a height of $h_9$, while the ridge 134 may protrude from the first surface 132 by a height of $h_{10}$. Generally, $h_9$ and $h_{10}$ may be the same or different. According to certain embodiments, it may be desirable for $h_9$ and/or $h_{10}$ to have a size that facilitates recognition by a user and that also blocks the connection region 50 from mating with the mating connector 56 when the electrical connector 48 is not properly positioned with respect to the mating connector 56. As illustrated, the ridge 134 and the groove 138 may be substantially centered about their respective surfaces. However, it should be appreciated that the ridge 134 and/or the groove 138 may be disposed about any location of their respective surfaces. Furthermore, it should be noted that any one or a combination of the approaches for inducing asymmetry into the electrical connector 48 may be used in combination with the approaches described with respect to FIG. 8. By way of non-limiting example, the embodiment of the insulating shroud 52 as described with respect to FIG. 6 may be modified to include the ridge 134 and/or the groove 138.

Figure 9:
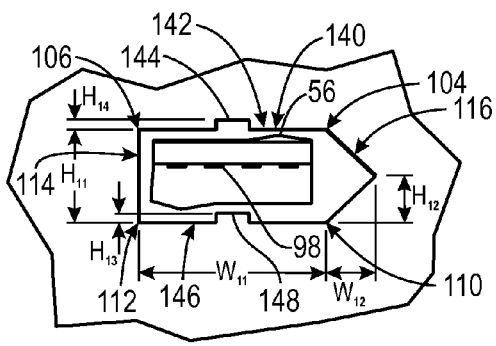
FIG. 9 is a front view of an embodiment of the mating connector and the receptacle of FIG. 3 illustrating an asymmetric geometry of the receptacle shaped to receive the connector and the insulating shroud of FIG. 8 along the connection axis, in accordance with an aspect of the present disclosure.

As discussed above, the mating connector 56 of the monitor 54 may have a geometry that matches (e.g., mirrors) the inner and/or outer geometries of the electrical connector 48 (including the insulating shroud 52 and the connection region 50). FIG. 9 illustrates a front view of an embodiment of the mating connector 56 having a receptacle 140 configured to enable connection with the electrical connector 48 of FIG. 8. As illustrated, the mating connector 56 may be shaped to minor the inner geometry 120. In particular, the receptacle 140 may include a first surface 142 having a ridge 144 corresponding to the ridge 134 of the connector 48 of FIG. 8 and a second surface 146 having a groove 148 corresponding to the groove 138 of the electrical connector 48 of FIG. 8. As may be appreciated, widths $w_{11}$ and $w_{12}$ and heights $h_{11}$, $h_{12}$, $h_{13}$, and $h_{14}$ may be suitably sized to accommodate widths $w_9$ and $w_{10}$ and heights $h_7$, $h_8$, $h_9$, and $h_{10}$ of the electrical connector 48 of FIG. 8.

Figure 10:
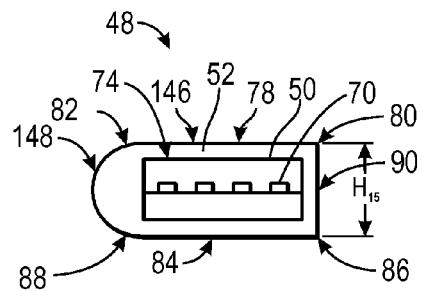
FIG. 10 is a front view of an embodiment of the connector and the insulating shroud of FIG. 2 illustrating an asymmetric geometry of the insulating shroud, in accordance with an aspect of the present disclosure.

In addition to, or in lieu of, any of the approaches described above, other embodiments of the insulating shroud 52 may include geometries having curved surfaces. For example, FIG. 10 illustrates a front view of the insulating shroud 52 including an outer geometry 146 with a curved fourth surface 148. As illustrated, the curved fourth surface 148 may be curved along its entirety. However, the curved fourth surface 148 may have a curved portion and a straight portion or several curved and straight portions (e.g., one or more "humps"). Additionally, the curved portion of the curved fourth surface 148 may have a constant or a varying radius. The curved fourth surface 148 may, in some embodiments, include multiple curved portions. In the illustrated embodiment, the curved fourth surface 148 may protrude from the second end 82 and the fourth end 88 of the first surface 78 and the second surface 84, respectively. However, in other embodiments, the curved fourth surface 148 may be curved inwardly (i.e., toward the connection region 50). As illustrated, the curved fourth surface 148 may be curved such that the outer geometry 146 may be asymmetric with respect to a plane that is crosswise to the connection axis 72 and that bisects the width of the connection region 50.

Figure 11:
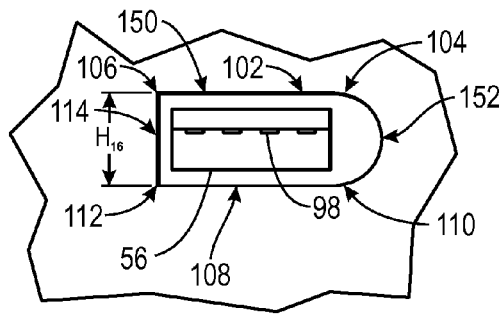
FIG. 11 is a front view of an embodiment of the mating connector and the receptacle of FIG. 3 illustrating an asymmetric geometry of the receptacle shaped to receive the connector and the insulating shroud of FIG. 10 along the connection axis, in accordance with an aspect of the present disclosure.

FIG. 11 illustrates a front view of an embodiment of the mating connector 56 having a receptacle 150 configured to enable connection with the electrical connector 48 of FIG. 10. The receptacle 150 may be shaped with dimensions corresponding to the outer geometry 146 to enable the insertion of the insulating shroud 52 into the receptacle 150. Additionally, the receptacle 150 may have surfaces and ends which are mirrored with respect to the outer geometry 146. Specifically, the receptacle 150 may have a curved fourth surface 152 which may be curved to correspond to the fourth surface 148 of the outer geometry 146.

Figure 12:
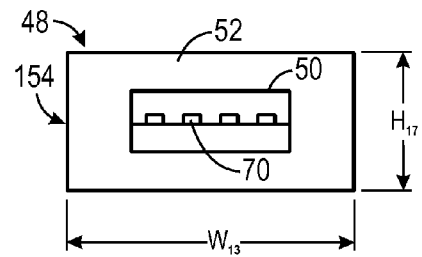
FIG. 12 illustrates a front view of an embodiment of the connector and the insulating shroud of FIG. 2 illustrating a symmetric geometry of the insulating shroud, in accordance with an aspect of the present disclosure.
Figure 13:
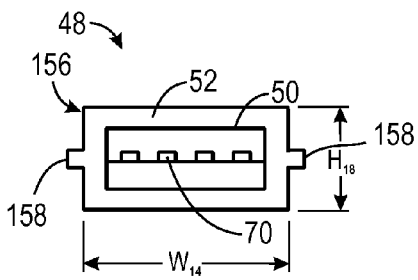
FIG. 13 illustrates a front view of an embodiment of the connector and the insulating shroud of FIG. 2 illustrating a symmetric geometry of the insulating shroud, in accordance with an aspect of the present disclosure.
Figure 14:
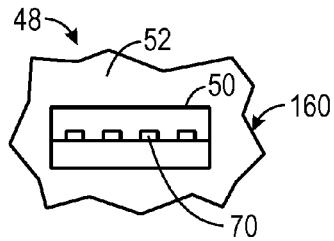
FIG. 14 illustrates a front view of an embodiment of the connector and the insulating shroud of FIG. 2 illustrating an asymmetric geometry of the insulating shroud, in accordance with an aspect of the present disclosure.

Additionally, as noted above, the insulating shroud 52 and/or the connection region 50 may include symmetric and/or asymmetric geometries that do not comply with the USB standard to enable connection with specific medical monitors (e.g., the monitor 54) having the mating connector 56. More specifically, the insulating shroud 52 and/or the connection region 50 may be shaped such that the electrical connector 48 may not be able to physically connect with a standard USB mating connector, such as the USB Series Standard-A, Standard-B, Mini-A, Mini-B, Micro-A, or Micro-B. For example, FIGS. 12-14 illustrate front views of embodiments of the insulating shroud 52 that do not comply with the USB standard. It should be noted that while the illustrated embodiments illustrate the insulating shroud 52 as having the geometries that do not comply with the USB standard, the connection region 50 may additionally or alternatively include the geometries. That is, the front view illustrated in FIGS. 12-14 may be front view of the connection region 50 of the electrical connector 48.

As illustrated in FIG. 12, the insulating shroud 52 may include a symmetrical outer geometry 154 having at least one dimension that does not match a corresponding dimension of any standard USB connectors. For example, the symmetrical outer geometry 154 may have a height of $h_{17}$ and a width of $w_{13}$, and $h_{17}$ and/or $w_{13}$ may be larger than the dimensions specified in the USB standard. The symmetrical outer geometry 154 may be square, rectangular, or any other suitable symmetric shape. For example, the symmetrical outer geometry 154 may include symmetrical angled sides such that the insulating shroud 52 is trapezoidal.

Additionally, as illustrated in FIG. 13, the insulating shroud 52 may include an outer geometry 156 that may have a height of $h_{18}$ and a width of $w_{14}$, which may be sized to physically couple with a USB mating connector in compliance with the USB standard. However, the outer geometry 156 additionally includes one or more tabs (e.g., protrusions or ridges) 158 that may not fit in the USB mating connector. As illustrated, the outer geometry 156 may be symmetrical. However, the outer geometry 156 may include an odd number of tabs 158 or an arrangement of tabs 158 to induce asymmetry in the outer geometry 156.

In another embodiment, as illustrated in FIG. 14, the insulating shroud 52 may include an irregular outer geometry 160. The irregular outer geometry 160 may include curved and/or angled portions in any combination.

Furthermore, it may be desirable to provide the electrical connector 48 with an embodiment of the insulating shroud 52 that does not comply with the USB standard and with an embodiment of the connection region 50 that does comply with the USB standard. More specifically, the dimensions and the geometry of the connection region 50 may comply with the USB standard such that the connection region 50 may physically couple to a standard USB port. Accordingly, in certain embodiments, the mating connector 56 of the monitor may also be shaped to comply with the USB standard, while the receptacle of the mating connector 56 may be shaped to receive the insulating shroud 52. Thus, the mating connector 56 may be configured to receive the connection region 50 of the electrical connector 48 and a standard USB device, such as a flash drive. However, in certain embodiments, the monitor 54 may be provided with only one mating connector 56 such that the monitor 54 may not be coupled to the electrical connector 48 and a standard USB device simultaneously. In this manner, the monitor 54 may not be coupled to a non-isolated device while coupled to the medical device (e.g., the tracheal tube 10). Alternatively, to enable simultaneous connection to the electrical connector 48 and a standard USB device, the monitor 54 may include more than one mating connector 56 and electrical isolation circuitry (i.e., an isolator) for each mating connector 56.

As described in detail above, the insulating shroud 52, and in particular, the asymmetry of the insulating shroud 52, may be desirable for a wide variety of electrical connectors 48 (e.g., a USB or a D-subminiature). For example, an embodiment of the insulating shroud 52 having a recessed configuration (e.g., a touchproof electrical connector 48) may block a user from inadvertently contacting the pins 70 disposed about the connection region 50. Additionally, the asymmetry of the insulating shroud 52 may enable a user to more easily determine the correct orientation of the electrical connector 48 for insertion into a corresponding mating connector. Furthermore, the asymmetry of the insulating shroud 52 may enable the electrical connector 48 to be used with a particular medical monitor having a corresponding mating connector and receptacle. Various embodiments of the asymmetry may be desirable to distinguish between different electrical connectors 48 and the corresponding medical monitor. By way of non-limiting example, a user may recognize the electrical connector 48 of FIG. 4 to be an electrical connector 48 suitable for use with the monitor 54 and the electrical connector 48 of FIG. 6 to be suitable for use with a pulse oximetry monitor.

However, in certain embodiments, it may be desirable to connect the electrical connector 48 having the insulating shroud 52 with a non-medical computing device lacking the electrical isolation circuitry in accordance with the medical electrical equipment standards of IEC-60601-1. For example, a user may desire to view images generated by the visualization device 24 on a standard computer. Additionally, a portable computing device (e.g., a laptop) may facilitate portable patient monitoring systems (e.g., transporting a patient).

Figure 15:
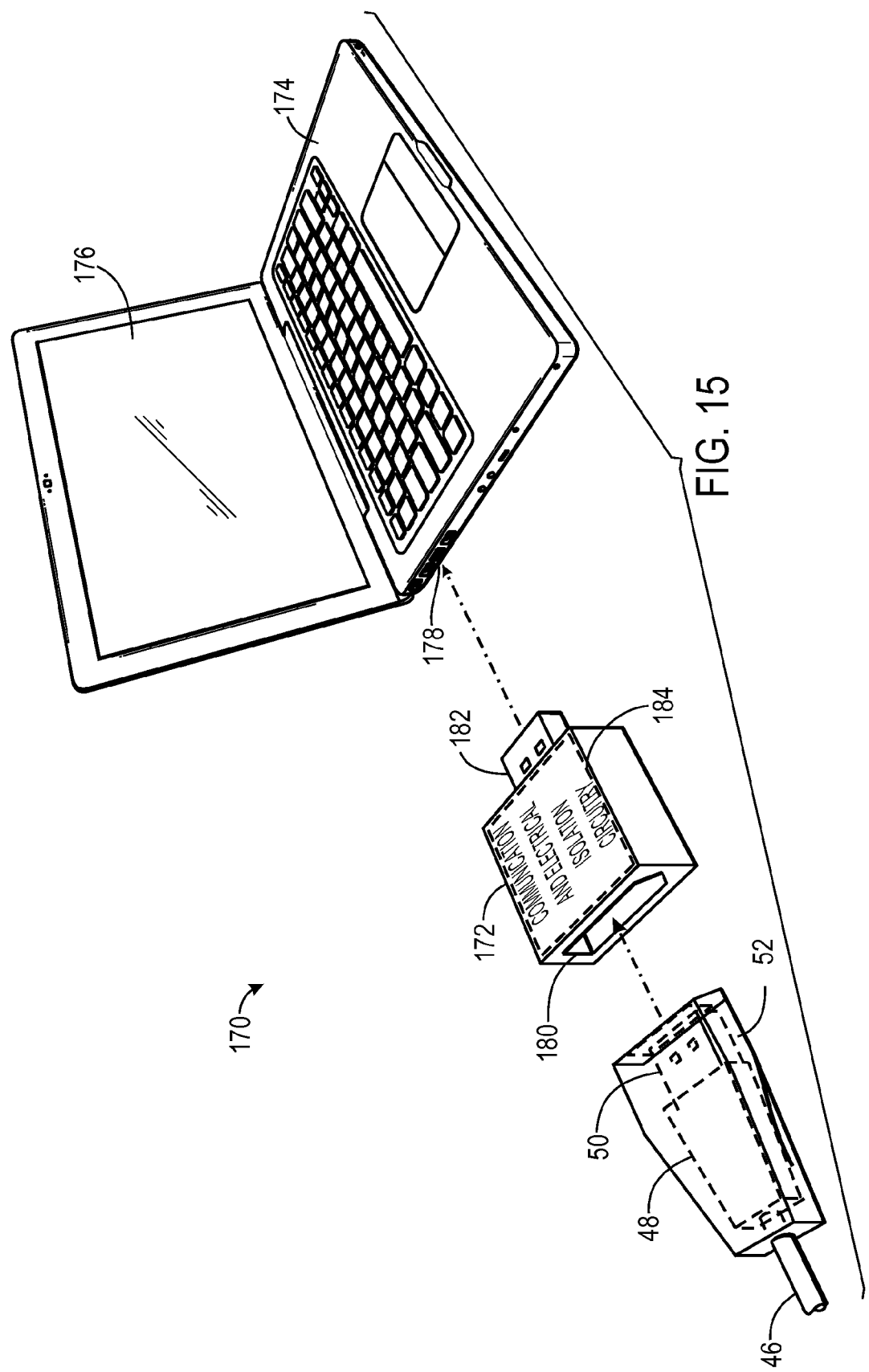
FIG. 15 is a perspective view of an embodiment of an adaptor configured to receive the connector and the insulating shroud of FIG. 2 and to connect with a computer having a mating connector and a receptacle shaped to receive the adaptor, in accordance with an aspect of the present disclosure.

With the foregoing in mind, FIG. 15 illustrates a system 170 which may include the electrical connector 48 having the insulating shroud 52, an adaptor 172, and a computer 174 (e.g., a portable computing device such as a laptop). The computer 174 may include a display 176 and one or more connection ports, such as a USB port 178. The computer 176 may include a processor (not shown) and one or more memory units (not shown). The processor of the computer 176 may be configured to execute code to process, analyze, and/or display data obtained by a medical device, such as for example, the visualization device 24 and/or a pulse oximetry sensor. Again, the computer 174 may not include electrical isolation circuitry in accordance with IEC 60606-1.

The adaptor 172 in accordance with present embodiments may be configured to perform one or more functions, such as enabling electrical coupling between the electrical connector 48 and the computer 174, and providing electrical isolation between a medical device to which the electrical connector 48 is attached and the computer 174. Specifically, the adaptor 172 may enable connection between two different types of connectors. As illustrated, the adaptor 172 is configured to receive the electrical connector 48 and the insulating shroud 52 via a receptacle 180. The receptacle 180 may function similar to the receptacles described with respect to FIGS. 5, 7, 9, and 11. Specifically, the geometry of the receptacle 180 may mirror that of the insulating shroud 52. The adaptor 172 also includes a connector 182 (e.g., a plug) configured to connect with a port of the computer 176. As illustrated, the connector 182 is a male USB connector configured to insert into the USB port 178. That is, in certain embodiments, the connector 182 may be include a geometry and dimensions in compliance with the USB standard to enable physical and electrical communication with a mating connector (e.g., the USB port 178) in compliance with the USB standard. However, it should be appreciated that as the computer 176 may include additional ports (e.g., VGA, S-Video, or serial port), the adaptor 174 may be modified to include an alternative connector 182, instead of the illustrated USB connector. Further, various adaptors 174 may be designed for various embodiments of the electrical connector 48 and the insulating shroud 52. Additionally, in other embodiments, the adaptor 172 may include a cable between the receptacle 180 and the connector 182.

The adaptor 174 also includes communication and electrical isolation circuitry 184. The communication circuitry 184 includes features (e.g., one or more pins) configured to receive signals from the electrical connector 48 and transmit the received signals to the computer 176. In certain embodiments, the adaptor 174 may merely provide a physical transformation. However, in other embodiments, the communication circuitry 184 may be configured to convert the signal received from the electrical connector 48 into a different signal type (e.g., a USB signal). The electrical isolation circuitry 184 may be desirable in circumstances in which the electrical connector 48 is connected to the computer 174 while a medical device (e.g., the tube 10 or a pulse oximetry sensor) coupled to the electrical connector 48 is obtaining data from a patient. Providing the electrical isolation circuitry 184 may enable the computer 174 to comply with the medical equipment standards in accordance with IEC 60606-1.

In one embodiment, the adaptor 172 having the communication and electrical isolation circuitry 184 may be configured to receive the electrical connector 48 without the insulating shroud 52. As noted above, in certain embodiments the connection region 50 of the electrical connector 48 may be constructed from an insulating material. Thus, the insulating shroud 52 may not be desired. However, providing an asymmetrical geometry for the electrical connector 48 may be desirable for the reasons described in detail above (e.g., for connecting with specific medical monitors and providing an indication of orientation). Accordingly, in one embodiment, the receptacle 180 of the adaptor 172 may be shaped to receive an asymmetrical geometry of the connection region 50. Furthermore, in embodiments in which the electrical connector 48 does not include the insulating shroud 52, the connection region 50 may be defined as an interface region, because the connection region 50 includes one or more surfaces which share a common boundary with one or more surfaces of a mating connector.

Figure 16:
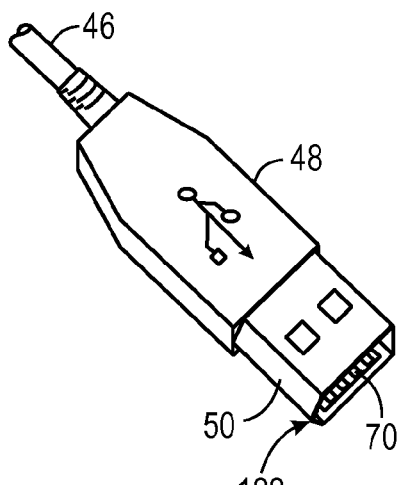
FIG. 16 is a perspective view of an embodiment of the connector of FIG. 1 illustrating an asymmetric geometry of the connection region, in accordance with an aspect of the present disclosure.

With the foregoing in mind, FIG. 16 illustrates an embodiment of the electrical connector 48 having the connection region 50 with an asymmetric geometry 188. As illustrated, the electrical connector 48 is a USB connector, which may be configured to communicate using the USB standard. However, it should be appreciated that the electrical connector 48 may be any electrical connector suitable for a medical device. Additionally, the connection region 50 may have various asymmetric and symmetric geometries, which may be similar to the various embodiments of the insulating shroud 52 as discussed above with respect to FIGS. 4, 6, 8, 10, and 12-14.

Figure 17:
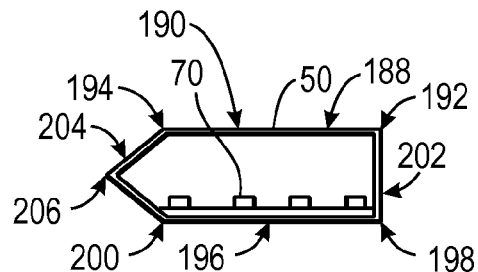
FIG. 17 is a front view of an embodiment of the connection region of the connector of FIG. 16 illustrating an asymmetrical geometry of the connection region, in accordance with an aspect of the present disclosure.

For example, FIG. 17 illustrates a front view of one embodiment of the connection region 50 having the asymmetric geometry 188. Specifically, as illustrated, the asymmetric geometry 188 may be similar to the outer geometry 76 of the insulating shroud 52 as illustrated in FIG. 4. Thus, the asymmetrical geometry 188 may include a first surface 190 terminating at a first and a second end 192 and 194, and a second surface 196 terminating at a third and a fourth end 198 and 200. A third surface 202 may connect the first and third ends 192 and 198 and may be substantially perpendicular to the first surface and the second surfaces 190 and 196. The third surface 202 may be an opposing surface with respect to a cornered fourth surface 204, as described above with respect to FIG. 4. The cornered fourth surface 204 may connect the first and second surfaces 190 and 192 at the second and fourth ends 194 and 200, respectively. The cornered fourth surface 204 may include a corner 206 such that the cornered fourth surface 204 may be angled away from the pins 70. In one embodiment, the cornered fourth surface 204 may be angled toward the pins 70. However, in other embodiments, the cornered fourth surface 204 may be angled toward the connection region 50. In certain embodiments, the electrical connector 48 may include the insulating shroud 52, which may be modified to fit about the asymmetric geometry 188 of the connection region 50.

Figure 18:
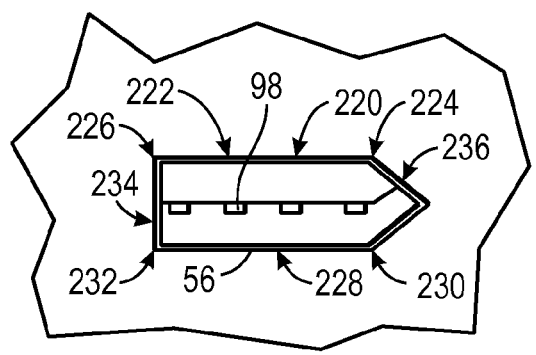
FIG. 18 is a perspective view of an embodiment of the mating connector of FIG. 3 that is shaped to receive the connector of FIG. 17, in accordance with an aspect of the present disclosure.

FIG. 18 illustrates a front view of an embodiment of the mating connector 56 having an asymmetric geometry 220, which may be configured to physically and electrically couple with the electrical connector 48 of FIG. 17. As illustrated, the asymmetric geometry 220 minors the asymmetric geometry 188 of the electrical connector 48 of FIG. 17. Specifically, the mating connector 56 includes a first surface 222 terminating at a first and a second end 224 and 226, and a second surface 228 terminating at a third and a fourth end 230 and 232. In a similar manner to the electrical connector 48 discussed above with respect to FIG. 17, a third surface 234 may be an opposing surface with respect to a cornered fourth surface 236. The cornered fourth surface 236 may connect the first and second surfaces 222 and 228 at first and third ends 224 and 230, respectively. In an embodiment in which the electrical connector 48 also includes the insulating shroud 52, a medical monitor (e.g., the monitor 54) having the mating connector 56 may additionally include a receptacle surrounding the mating connector 56 to enable insertion of the insulating shroud 52.

As discussed above, the embodiments discussed with respect to FIGS. 1-18 generally relate to an embodiment of the electrical connector 48 where the electrical connector 48 may include the insulating shroud 52 and/or the connection region 50 that may be shaped such that the electrical connector 48 does not comply with the USB standard. However, in other embodiments, the electrical connector 48 may not include the insulating shroud 52 and may include a connection region 50 in compliance with the USB standard and thus, may not be able to connect with medical monitors 34 having the mating connector 56. Furthermore, various medical monitors 34 may include mating connectors 56 with different geometries to enable connection with a variety of medical devices having electrical connectors 48 with different geometries. As such, the electrical connector 48 may have a different geometry than the mating connector 56. Accordingly, it may be desirable to provide a dongle that is configured to connect the medical device to the medical monitor 34.

FIG. 19 illustrates a perspective view of a system 250 including the electrical connector 48. In the illustrated embodiment, the electrical connector 48 does not include the insulating shroud 52. Furthermore, the electrical connector 48 may include the USB pin-out 66 and the connection region 50 that complies with the USB standard. For example, the connection region 50 may be a Series A USB connector. The system 250 also includes a dongle 252. The dongle 252 may include a receptacle 254 (e.g., a mating connector) shaped to receive the connection region 50. Accordingly, the receptacle 254 may also comply with the USB standard. The dongle 252 may also include a connector 256 (e.g., a plug) that is configured to connect with an embodiment of the mating connector 56. In certain embodiments, the dongle 252 may be configured to enable communication between the tracheal tube 10, or another medical device such as a sensor, and the medical monitor 34 according to the USB standard. Additionally, in certain embodiments, the dongle 252 may include a cable 258 between the receptacle 254 and the connector 256. The cable 258 may be advantageous to provide additional length so the tracheal tube 10 (or another medical device) may be placed at a distance away from the monitor 34. Alternatively, the receptacle 254 and the connector 256 may be disposed in a single unit, similar to the illustrated embodiment of the adaptor 172. To enable connection with the mating connector 56, the connector 256 may include a geometry 260 that does not comply with the USB standard. In certain embodiments, the connector 256 may prevent the dongle 252 from connecting to a mating connector that complies with the USB standard (e.g., a USB port). Furthermore, it should be noted that the connector 256 may include the insulating shroud 52, and thus, the insulating shroud 52 may additionally or alternatively include the geometry 260. As illustrated, the geometry 260 is similar to the asymmetric geometry 188 of FIG. 15. However, the geometry 260 may be any of the geometries described above.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to the connector types as illustrated, but these techniques may also be utilized for other connector types suitable for medical devices. Additionally, any of the disclosed asymmetrical geometries, may include additional asymmetrical surfaces. For example, an embodiment of an asymmetrical geometry may include some combination of the described fourth surfaces. Rather, the various embodiments may cover all modifications, equivalents, and alternatives falling within the spirit and scope of the disclosure as defined by the following appended claims.

What is claimed is:

1. A system, comprising:
a sensor comprising one or more electrical components configured to collect data relating to a patient, wherein the sensor is electrically coupled to a connector via a cable, and wherein the connector is configured to receive the data from the one or more electrical components; and
a dongle configured to enable communication between the sensor and a patient monitor such that the communication complies with a Universal Serial Bus (USB) standard and comprising:
a receptacle configured to couple to the connector of the sensor;
a plug configured to couple to a mating connector of the patient monitor, wherein the plug comprises a geometry or a dimension that does not comply with the USB standard; and
a cable coupling the receptacle with the plug.

2. The system of claim 1, wherein the sensor comprises a visualization device disposed on or within an endotracheal tube.

3. The system of claim 1, wherein the plug prevents the dongle from connecting to a USB port in compliance with the USB standard.

4. The system of claim 1, wherein the dongle comprises at least a portion of an insulating shroud disposed about the plug, wherein at least a portion of the plug is conductive and the insulating shroud is formed from an insulating material.

5. A medical system, comprising:
a sensor comprising one or more electrical components configured to collect data relating to a patient, wherein the sensor is electrically coupled to a connector via a cable, and wherein the connector comprises one or more contacts configured to receive the data from the one or more electrical components and to enable communication between the sensor and a medical monitor such that the communication complies with a Universal Serial Bus (USB) standard; and
the medical monitor configured to receive the data collected by the sensor to monitor one or more physiological parameters of the patient; and
wherein the connector comprises an interface region disposed at least partially about the one or more contacts and configured to enable the connector to physically couple to a mating connector of the medical monitor, wherein the interface region comprises a geometry or a dimension that does not comply with the USB standard, and wherein the medical monitor comprises the mating connector having substantially the same geometry and dimensions as the interface region of the connector of the sensor.

6. The medical system of claim 5, wherein the sensor comprises a visualization device disposed on or within an endotracheal tube.

7. The medical system of claim 5, comprising an adaptor, wherein the adaptor comprises:
a receptacle configured to receive the connector of the sensor;
electrical isolation circuitry configured to electrically isolate the patient from an earth ground; and
a plug configured to electrically and physically couple to a port of a computing device.

8. The medical system of claim 7, wherein the plug of the adaptor comprises a geometry and dimensions in compliance with the USB standard, and wherein the port of the computing device comprises a USB port in compliance with the USB standard.

9. The medical system of claim 5, wherein the interface region comprises a first surface and a second surface disposed on opposite sides of the one or more contacts, wherein the first and second surfaces are not parallel and have different respective lengths.

10. The medical system of claim 5, wherein the interface region comprises a height or a width that is larger than a height or a width, respectively, specified by the USB standard.

11. A medical system, comprising:
a sensor comprising one or more electrical components configured to collect data relating to a patient, wherein the sensor is electrically coupled to a connector via a cable, and wherein the connector comprises:
one or more contacts configured to receive the data from the one or more electrical components and to enable communication between the sensor and a medical monitor such that the communication complies with a Universal Serial Bus (USB) standard;
an interface region disposed at least partially about the one or more contacts, wherein the interface region comprises an inner interface region with a first geometry that complies with the USB standard and an outer interface region with a second geometry that does not comply with the USB standard; and
the medical monitor having a mating connector, wherein the mating connector comprises an inner mating region comprising the first geometry and an outer mating region comprising the second geometry.

12. The medical system of claim 11, wherein the outer interface region is formed from an insulating material.

13. The medical system of claim 12, wherein the inner interface region is conductive and the outer interface region extends past the inner interface region.

14. The medical system of claim 11, wherein the sensor comprises a visualization device disposed on or within an endotracheal tube.

15. The medical system of claim 11, wherein the outer interface region comprises a height or a width that is larger than a height or a width, respectively, specified by the USB standard.

16. The medical system of claim 11, wherein the outer interface region comprises a first surface and a second surface opposite the first surface, wherein the first and second surfaces are not parallel and have different respective lengths.

17. The medical system of claim 11, wherein at least one surface of the outer interface region comprises a ridge or a groove.

* * * * *